United States Patent
Vereecken et al.

(10) Patent No.: US 6,275,645 B1
(45) Date of Patent: Aug. 14, 2001

(54) METHOD OF AND APPARATUS FOR SUBSURFACE EXPLORATION

(75) Inventors: Harry Vereecken, Julich; Jürgen Höltkemeier, Niederzier, both of (DE)

(73) Assignee: Forschungszentrum Julich GmbH, Julich (DE)

( * ) Notice: Subject to any disclaimer, the term of this patent is extended or adjusted under 35 U.S.C. 154(b) by 0 days.

(21) Appl. No.: 09/333,349

(22) Filed: Jun. 15, 1999

(30) Foreign Application Priority Data

Jun. 15, 1998 (DE) .............................................. 198 26 265

(51) Int. Cl.$^7$ ....................................................... G02B 6/00
(52) U.S. Cl. ........................... 385/147; 250/254; 250/255; 250/256
(58) Field of Search ............................ 385/147; 250/254, 250/255, 256

(56) References Cited

U.S. PATENT DOCUMENTS

| | | | | |
|---|---|---|---|---|
| 4,609,821 | * | 9/1986 | Summers ............................. | 250/255 |
| 5,128,882 | * | 7/1992 | Cooper et al. ...................... | 364/550 |
| 5,316,950 | * | 5/1994 | Apitz et al. ........................... | 436/28 |
| 5,759,859 | * | 6/1998 | Sausa ................................... | 436/106 |
| 5,902,939 | * | 5/1999 | Ballard et al. .................... | 73/863.12 |

* cited by examiner

Primary Examiner—Rodney Bovernick
Assistant Examiner—Sung Pak
(74) Attorney, Agent, or Firm—Herbert Dubno

(57) ABSTRACT

A method and probe for subterranean determination of the concentration of a substance has a light-conducting optical fiber running from above the ground to a measurement cell below the ground. The system can be used effectively for fluorescent markers to track the ground water flow.

11 Claims, 1 Drawing Sheet

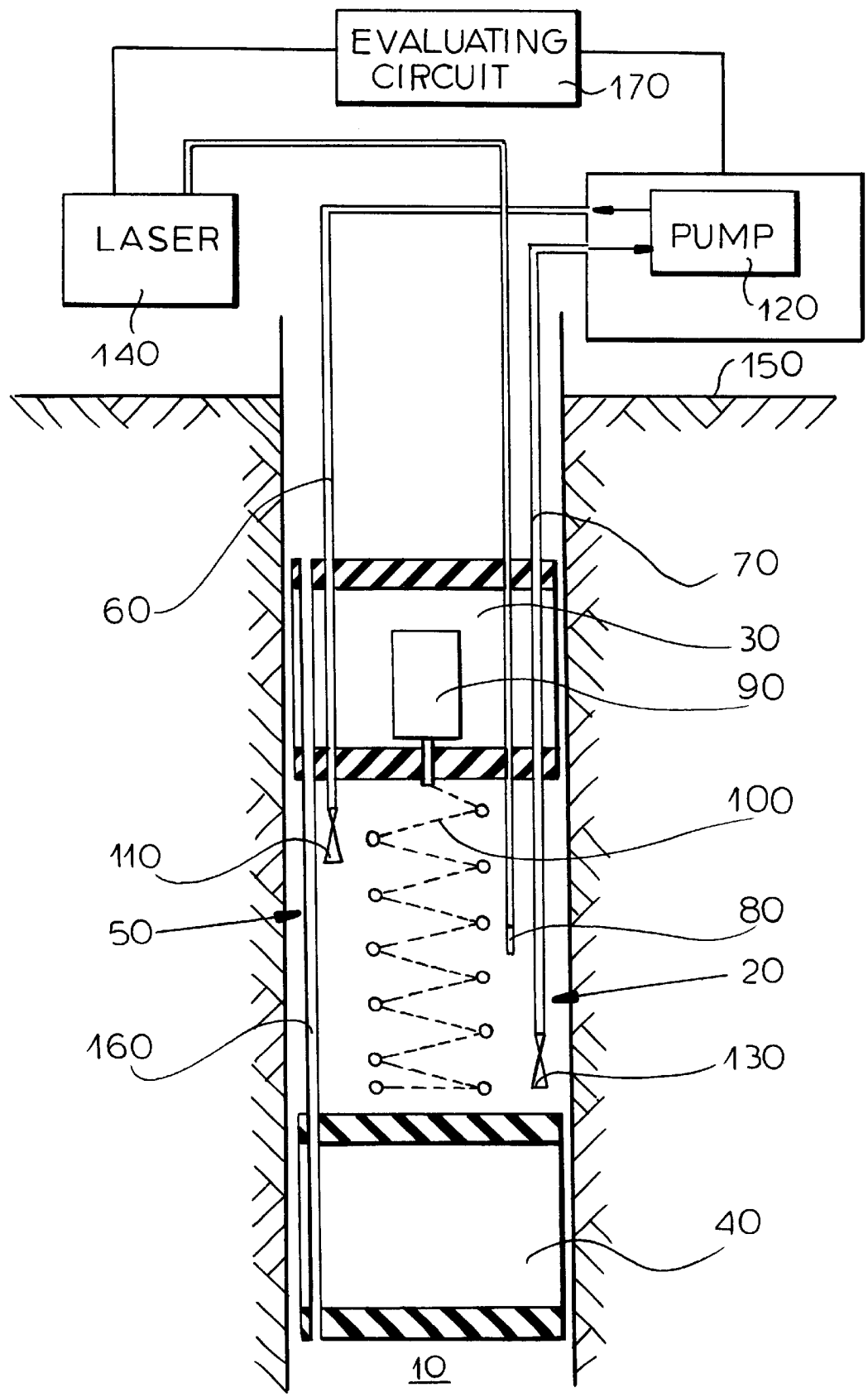

METHOD OF AND APPARATUS FOR SUBSURFACE EXPLORATION

FIELD OF THE INVENTION

The present invention relates to a subsurface exploration method and apparatus which allows a concentration of at least one substance to be determined at a below-ground region. More particularly, the invention relates to a method of subsurface exploration in which a substance normally present at a particular below-ground region is monitored or has its concentration detected and to an apparatus for this purpose.

BACKGROUND OF THE INVENTION

Subsurface exploration can be desirable for a large number of reasons and can serve for a wide variety of purposes. For example, one may wish to detect the presence, concentration, change of concentration or the like of a substance which is naturally present at a particular below-ground region, or a substance which may appear at such a region because of leeching or migration from another location, as in the case of monitoring waste disposal sites, or one may wish to determine the concentration of a marker substance introduced into the region as an indication of migration of materials through the region. For this purpose, it is customary to provide a well or bore hole and a monitoring unit in the cell or bore holes.

One process for subsurface exploration in which at one location in the ground at least one marker substance is introduced, has been described by M. Schöttler in: "Entwicklung eines Einbohrlock-Verfahrens zur Messung horizontaler Grundwasserströmungen" lines 19, 20 of page 1, (Development of a Single Borehole Process for Measurement of Horizontal Ground Water Flows).

In this article, a borehole probe is described for carrying out the process. The borehole probe operates with a measurement cell which contains two light sources, a lens system and a special video camera. A marker substance (tracer) of a material capable of fluorescence is liberated centrally over an observation region on which the system is focussed with a focal length of several millimeters. This region lies axially centrally of the measurement cross section and is freely traversable by the flow to be measured. Light emitted from the light sources are re-emitted light of shifted wavelength from the marker are registered by the video camera as bright image points. A contrasting image point is found on an image plane captured by video techniques.

This borehole probe and the process by which it is used and is effective can be provided in standard 10 cm (4 inch) wide boreholes.

Another borehole probe from GSF Munich, Germany, can detect the movement of radio-active marker substances. For this purpose, however, it is necessary to make use of a short-lived isotope which must be produced in a nuclear reactor. This process is relatively expensive. In addition, because the marker substance has a relatively short life, it is sensitive to storage time and it is difficult to keep available quantities of the marker in stock.

The University of California has developed a bore hole probe in which a sample is pumped from the subterranean region of an above-ground location. This system does not permit in situ measurement.

The Technical University of Freiburg, Germany has also developed a bore hole probe. This system operates with heat pulses and has been found to be suitable only for the determination of high ground water speeds.

OBJECTS OF THE INVENTION

It is, therefore, the principal object of the present invention to provide a simple, versatile, reliable and economical process for subsurface exploration which will avoid the drawbacks of earlier systems.

Another object of this invention is to provide an improved apparatus for determining the concentration, in situ of a substance in a below-ground region.

Still another object of this invention is to provide a method of and an apparatus for subsurface exploration which can be used to monitor or determine a wide range of ground water velocities than has been possible heretofore, which does not require generation of a radio-active isotope, and which is free from the need for specialized video cameras or the like.

Still another object of this invention is to provide a subsurface exploration probe which can be of low cost.

SUMMARY OF THE INVENTION

These object and others which will become apparent hereinafter are attained, in accordance with the invention, in a system in which at least at one below-ground region, at least one substance is so excited by electromagnetic radiation to which that substances is subjected that it will, in turn, emit electromagnetic radiation. Either that re-emitted radiation or the originally introduced radiation is conducted via a waveguide at least in part between the below-ground region and the region at which the electromagnetic energy is generated and/or analyzed.

According to the invention, the process is so carried out that a coupling in and/or the coupling out of the electromagnetic energy with respect to the below-ground region is effected via a light-conducting or optical fiber.

Advantageously, the electromagnetic radiation includes a light beam which can have an emission wavelength between 200 nm and 950 nm. The substance which is detected in this manner is a substance which can be excited by the light radiation, preferably so as to be luminescent. In this case, an energy absorption takes place via atoms, molecules or condensed material, whereas the emission can be either a phosphorescence or a fluorescence which is detected by the out-coupling of the re-emitted light to the measurement location. While the re-emitted light is evaluated externally of the borehole, the fact that the light is transmitted out of the region for evaluation does not change the fact that the measurement is in situ at the region and is carried out with a high time resolution.

According to a feature of the invention, a bore hole probe can be provided to measure concentration of a substance in the ground and has at least one means for coupling the electromagnetic radiation to the region and/or coupling electromagnetic radiation out of the region, such means including a light-conductive fiber. Especially small dimensions of the probe can be obtained when the light-conducting fiber serves both as the means for coupling the electromagnetic energy into and out of the system.

For detecting flow velocity of nonfluorescent substances it is advantageous to introduce into the region a marker substance, preferably from an upper location in the bore hole. A homogeneous distribution of the substance to be measured can be obtained by providing a mixing device as part of the bore hole probe in the bore hole.

The light beam can be generated by a laser. It has been found to be advantageous to provide the laser above ground, although it can be provided in the bore hole. In this case a relatively bulky laser can be used which has particularly desirable emission characteristics, allowing it to cover both UV and visible ranges.

It is possible, in accordance with the invention, to utilize a very compact laser. With a highly compact semiconductor laser, in the form, for example, of a pn laser diode in which the pn transition serves as a pump for the laser, the active (amplifying) material is formed by a semiconductor with a direct band gap. The active region of the laser diode is a thin laser in the direct vicinity of the space charge region of the pa transition. The laser diode emits coherent radiation with the line widths of the order of magnitude of 0.1 nm and with sharp directionality.

A further suitable light source for incorporation in the bore hole probe is a luminescence diode (LED, light emitting diode). The luminescence diode contains a semiconductive material with a p-doped region and an n-doped region. Excess charge carriers provided in these regions diffuse respectively in each other region and recombine there as its charge carriers. The result is an incoherent electromagnetic radiation with a duplicate line width of the order of magnitude of several 10 nm. The band width depends upon the selection of the semiconductive material and its doping.

For the best possible separation between emitted light and re-emitted light from the excited substance, it is advantageous to utilize a monochromatic light as the exciting source. An especially reduced band width of preferably less than 10 nm and especially of about 0.1 nm has the advantage that the spectral distribution can be maintained as exactly as possible. A shifting of the wavelength between emitted and re-emitted light is thus usually between 20 nm and about 100 nm. It is also advantageous to use a light source which has emission characteristics capable of being varied with time. With such time-variable emission characteristics, an intensity modulation can be provided or a modulation of the wavelength of the emitting radiation can be obtained. With the use of a CCD camera, it is possible to detect a decay process of the excitation.

The use of a light source with a time-variable emission wavelength enables different materials in the ground to be excited to emission and to separate them from one another.

One application of the invention is an in situ determination of a flow velocity of a liquid, especially a ground water stream. However, the invention should not be understood to be limited any way to this specific example. With the aid of the process of the invention and/or a bore hole probe according to the invention, it is possible to determine a depth profile of a concentration and/or a flow velocity of a material.

It is also a feature of the invention that it can be used to detect a raw material.

The process of the invention, moreover, is so robust that it can be used for long-duration investigation for a targeted monitoring of concentrations and/or flow velocity. It is, for example, possible to provide one or more bore hole probes according to the invention in the region of a waste deposit site (dump) in selected regions of such a site, to detect whether there is a diffusion of contaminants into the ground water.

The process of the invention and the bore hole probe can also be used elsewhere in which a limited range of concentrations, concentration changes or flow velocities must be detected. Instead of a pulsed laser a continuous laser can be used. A typical pulse duration of a pulsed laser amounts to about 0.5 ns. In the spectral analysis of the recovered signal, the intensity of the signal is determined as the function of the wavelength. It has been found to be especially advantageous to carry out a calibration measurement with a system with known parameters so that not only qualitative changes can be determined via the single intensity but also quantitative values can be ascertained.

BRIEF DESCRIPTION OF THE DRAWING

The above and other objects, features, and advantages will become more readily apparent from the accompanying, drawing, the sole FIGURE of which is a diagrammatic view of a bore hole probe for carrying out the invention.

SPECIFIC DESCRIPTION

The drawing, which is not to scale, is intended to show a bore hole 10 in the vicinity of a waste disposal site or dump and in which a bore hole probe 20 is provided. The bore hole probe 20 comprises two packers 30 and 40 between which a measurement cell 50 is provided, the measurement cell being defined between the upper backer 30 and the lower packer 40. This region 50 is also defined as the below-ground region in which the measurement takes place.

The upper packer 30 is a passage for a supply line 60 and a passage for a discharge line 70, in addition to a passage for a light-conducting optical fiber 80 which can be enclosed within a glass fiber cable.

In the packer 30, moreover, a motor 90 is mounted to drive a mixing spiral or screw 100 which, upon rotation, thoroughly mixes the liquid in the region 50 between the two packers.

The mixer can have any other configuration which may be advantageous and/or desirable to effect thorough mixing within the region 50. The mixing should be such that it renders the composition in the region 50 homogeneous even when a liquid is injected at high speed therein.

The feed line 60 is provided with a valve 110 which controllably admits a marker substance into the measurement cell 50, the marker substance being delivered by a pump 120. The discharge line 70 has a foot valve 130 allowing liquid to drained back to the intake side of the pump 120. The optical fiber 80 is connected to a laser source 140 and both the laser source and the pump can be connected to an evaluating circuit 170 which, like the laser and the pump, are located above ground as represented at 150.

The laser 140 can be a dye laser with an emission wavelength between 360 nm, and 990 nm and which, in turn, can be excited or pumped by a nitrogen laser with an emission wavelength of 337.1 nm. Between the light waveguide 80 and the dye laser, a frequency multiplier (SHG) can be provided. The SHG unit can be a unit with a BBO crystal, a reflector and two lenses and, in that case, the SHG unit can effect a frequency doubling of the dye laser signal to provide an output wavelength of preferably 220 nm to 360 nm.

Other constructions of the laser can be used as well, as long as the laser can excite the substance in the cell 50 and the light waveguide 80 can conduct secondary emissions or re-emitted signals from this region for evaluation above ground.

While the laser is relatively bulky, that normally will pose no problem because it can be built in with its evaluating circuit into a common housing with the spectrometer used for analysis of the re-emitted light signal. For connection of the spectrometer and the laser, a Y-coupling can be provided for the optical fiber 80.

Depending upon the choice of the laser system, it is possible to vary the excitation wavelength between 200 nm and 950 nm. The reference numerals 140 and 170 not only encompass the laser and the evaluating circuitry but represent the spectrometer as well. A bypass duct 160 passes through the probe in the vertical direction to ensure that the vertical flow through the system will not interfere with the transverse flow and hence measurement of transverse liquid movements by the probe.

The probe 20 can be inserted into bore holes of a diameter of 5 cm (2 inches).

According to the invention, a test bore is produced in the vicinity of the dump to the depth of the aquifer and the probe is fixed at this depth in a filter region of the bore hole 108 using packers 30 and 40, a measurement region 50 is defined which is so isolated that only transverse flow through this region can occur. Bypass 160 allows vertical flow in the bore below bypassing the probe 20 without influencing the horizontal movement of liquid.

The measurement commences with the liberation of a marker substance in the region 50. The marker substance can be a uranium solution which is fed by the line 60 and the valve 110 into the measurement region 50. The uranium solution is a dye stuff which, contrary to what is implied in its name, is not radio-active but rather is provided in the form of a carboxylic acid derivative. The particular form of the uranium depends upon the pH of the solution in which the uranium is provided. Uranium even in very small concentrations, which can be less than 0.002 $\mu$g/l, can be effective for measurement purposes. The quantum yield and thus the amplitude of the fluorescence is extraordinarily high. Because of the low detection limit uranium has the further advantage that its calibration curve can be substantially linear over 5 concentration ranges (orders of magnitude). Only at very high concentrations above 10,000 $\mu$g/l, does the florescence intensity decrease as a result of intrinsic absorption and reduced dissociation. The marker substance introduced into the region 50 is homogeneously distributed therein by means of the motor 90 and the mixing spiral 100 driven thereby.

Ground water flowing transversely through the well entrains the marker substance into the surrounding ground strata and replaces the marker substance by water, thereby decreasing the measured concentration in the well 50 as a function of the ground water velocity.

The laser light emitted in the cell is delivered to the light waveguide 80 and conducted to the laser unit 140 and evaluated by the circuit 170. The changing concentration can be read out immediately as a measurement of horizontal ground water flow. The system is thus a single well detector for ground water flow as described. The concentration measurement can also be used to detect specific fluorescent substances and can also be part of a multi-well measurement system.

Other sensors can be introduced, e.g. for pH value, electrical conductivity, temperature or chemical concentrations of substances, especially oxygen, so that the probe can be a multiparameter probe as well.

The probe is especially effective for use in upper parts of below-ground regions and can be effective to respond to the changes in the feeding of marker substances thereto, although it is also effective at considerable depths.

The term "ground" is used here in its most general sense to mean not only the geological formations but all parts of structures in which wells and probes can be provided. For example the probes of the invention can be provided directly within a dump or along the periphery of a dump and practically any kind of dump may be monitored, especially municipal refuse dumps and the like in which there is the danger of contaminants reaching ground water.

The probe can also be used along roadways where there is a similar danger.

We claim:

1. A subsurface exploration method which comprises the steps of:

(a) In a bore hole extending from ground level to a below-ground location, delimiting a chamber in the bore hole between upper and lower packers;

(b) providing in said chamber a substance capable of excitation by a certain electromagnetic energy to cause re-emission of electromagnetic energy to cause re-emission of electromagnetic energy by the substance;

(c) coupling said certain electromagnetic energy into said chamber between said upper and lower packers, thereby causing said substance to re-emit electromagnetic energy in said chamber;

(d) coupling re-emitted electromagnetic energy out of said chamber to a measurement location;

(e) guiding electromagnetic energy at least partway between said chamber and said measurement location and at least in a vicinity of said chamber with at least one electromagnetic energy waveguide; and (f) determining the concentration of said substance in said chamber from re-emitted electromagnetic radiation therefrom.

2. The method defined in claim 1, further comprising the step of mixing said substance into contents of said chamber between said packers.

3. The method defined in claim 1 wherein said electromagnetic energy waveguide is a light-conducting optical fiber and said electromagnetic energy is a light beam.

4. The method defined in claim 3 wherein said light beam has an emission wavelength between 200 nm and 950 nm.

5. The method defined in claim 4, further comprising the step of generating said light beam by a laser.

6. The method defined in claim 5 wherein said certain electromagnetic energy is coupled into said chamber and said re-emitted energy is coupled out of said chamber through a common optical fiber extending from said chamber to said level.

7. A subsurface exploration apparatus for a bore hole extending from ground level to a below ground region comprising:

upper and lower packers in said bore hole delimiting a chamber therein containing a substance capable of excitation by a certain electromagnetic energy to cause re-emission of electromagnetic energy by said substance;

means for coupling electromagnetic energy into said chamber to excite said substance and cause said substance to re-emit electromagnetic energy;

means for coupling re-emitted electromagnetic energy out of said chamber to a measurement location, at least one of said means including a light-conducting fiber forming a waveguide for guiding electromagnetic energy at least partway between said chamber and said measurement location and at least in a vicinity of said chamber; and means connected with said waveguide for determining a concentration of said substance in said chamber from re-emitted electromagnetic radiation from said substance.

8. The apparatus defined in claim 7, further comprising a device in said chamber for mixing said substance with contents of said chamber.

9. The apparatus defined in claim 8 wherein the light-conducting fiber is connected to couple light energy into said chamber and to couple re-emitted light energy out of said chamber, said apparatus comprising a laser connected to said light-conducting fiber.

10. The apparatus defined in claim 9, further comprising bypass means connecting locations above and below said chamber to permit passage of liquid therebetween without interference with transverse flow through said chamber.

11. The apparatus defined in claim 10 wherein said bore hole is located in a region of a waste disposal site.

\* \* \* \* \*